United States Patent [19]
Grob et al.

[11] Patent Number: 5,241,367
[45] Date of Patent: Aug. 31, 1993

[54] DEVICE FOR MEASURING THE COMPOSITION OF FLUIDS, IN PARTICULAR THE COMPONENTS OF EXHAUST GASES FROM INTERNAL COMBUSTION ENGINES

[75] Inventors: Ferdinand Grob, Besigheim; Hubert Dettling, Waiblingen-Hohenacker; Heinz Stutzenberger, Vaihingen/Enz; Roger Potschin, Brackenheim, all of Fed. Rep. of Germany

[73] Assignee: Robert Bosch GmbH, Stuttgart, Fed. Rep. of Germany

[21] Appl. No.: 730,780

[22] PCT Filed: Jan. 17, 1991

[86] PCT No.: PCT/DE91/00026
§ 371 Date: Jul. 24, 1991
§ 102(e) Date: Jul. 24, 1991

[87] PCT Pub. No.: WO91/11702
PCT Pub. Date: Aug. 8, 1991

[30] Foreign Application Priority Data
Feb. 3, 1990 [DE] Fed. Rep. of Germany ....... 4003176

[51] Int. Cl.⁵ ................. G01N 21/59; G01N 21/85
[52] U.S. Cl. .................... 356/435; 250/575; 356/438; 356/439
[58] Field of Search ............. 356/435, 436, 437, 438, 356/439, 440; 250/573, 575, 565

[56] References Cited

U.S. PATENT DOCUMENTS

| | | | |
|---|---|---|---|
| 3,141,094 | 7/1964 | Strickler | 356/440 X |
| 3,885,162 | 5/1975 | Geertz | 250/573 |
| 3,994,590 | 11/1976 | Di Martini et al. | 250/565 X |
| 4,432,649 | 2/1984 | Krause | 356/438 |
| 4,544,273 | 10/1985 | Berndt | 356/437 X |
| 4,713,964 | 12/1987 | Ioannides | 356/439 X |
| 4,746,218 | 5/1988 | Lord, III | 356/437 |
| 5,004,349 | 4/1991 | Sato et al. | 356/402 |
| 5,009,064 | 4/1991 | Grob et al. | 60/273 |

FOREIGN PATENT DOCUMENTS

| | | |
|---|---|---|
| 2022736 | 11/1970 | Fed. Rep. of Germany . |
| 2945608 | 5/1981 | Fed. Rep. of Germany . |
| 3839348 | 6/1989 | Fed. Rep. of Germany . |
| 62-24131 | 2/1987 | Japan . |

Primary Examiner—Vincent P. McGraw
Attorney, Agent, or Firm—Felfe & Lynch

[57] ABSTRACT

A device is proposed for measuring the composition of fluids, in particular of constituents of exhaust gases from internal combustion engines, in which a light ray (32, 31) is used to irradiate the exhaust gas to be measured over the length of a measuring section (29) and is weakened or changed more or less, depending on the content of constituents. The light signal being received is advantageously registered by a measured length light receiver (18) which is shielded light-tight against the light emitting light source (14) and is evaluated in relation to the original light emission, in an evaluation circuit (26). In this simple way, accurate information is obtained of the exhaust gas clouding and of the loading of a fluid or gas with constituents which are optically active.

8 Claims, 1 Drawing Sheet

DEVICE FOR MEASURING THE COMPOSITION OF FLUIDS, IN PARTICULAR THE COMPONENTS OF EXHAUST GASES FROM INTERNAL COMBUSTION ENGINES

STATE OF TECHNOLOGY

The invention relates to a device for measuring the composition of fluids, in particular the components of exhaust gases from internal combustion engines. In such a device known through DE-OS 20 22 736, the light conductive bodies lead to spatially widely differing locations, with the light conductive bodies being of flexible make-up. The device is designed in such a way that a part of the light conductive bodies, together with the reflecting arrangement, is immersed in the medium which is to be measured. A further proposal suggests that the individual components of the generic type be gathered together in one single arrangement so that a compact arrangement is obtained, but this presents the difficulty that the light source will impart its light not only to the reference light receiver directly, but also to the measuring path light receiver, which would lead to a falsification of the measured result.

ADVANTAGES OF THE INVENTION

In contrast, the device in accordance with the invention has the advantage that it is of very compact construction and operates with great sensitivity, eliminating stray light and providing accurate measured results. Advantageous further developments of the device in accordance with the invention are identified by the subordinate claims. According to claims 2 and 3, a measuring error is advantageously avoided by either controlling the light source to a constant value or by comparing the actual light emission directly with the measured value of the light receiver for the measured length. A drop in the light output of the light source can be directly compensated in this arrangement.

The embodiment in accordance with claim 4 makes it possible for the light emitted from the light source to be very accurately detected, since a distribution of the reference light receiver to several receivers can detect the spatially radiated light output more accurately.

The embodiment in accordance with claim 5 provides a statistic mean value of the measured result in which it is possible for influences which affect the light transmission in only one direction, and most importantly, heat influences which can occur on one side, to be compensated.

In a simplified way, this can also be achieved with the embodiment in accordance with claim 6, and in both cases, it is also possible in the long term to take into account influences of the structural members, the light source or the light receiver, and for example, to keep drifts which are accounted for by ageing influences, small. Preferably, however, an even thermal loading of the optically active components, the light source and/or light receiver, is achieved which in turn reduces drift occurrences.

The embodiment in accordance with claim 7 provides for advantageous ascertainment of components in the fluids which cause a specific light absorption of the light cast on them. With the use of differing light wave lengths, components in the fluids can be measured selectively and accurately, which will have a particularly intensive retroaction on these particular light wave lengths. Due to its physical properties, the particular light source can, upon stimulation, produce an intensified special light source emission, or, the special light source emission will be caused by the downstream arrangement of optical filters. The equivalent will apply to light receivers.

A further advantageous embodiment is that of claim 9, in which a very compact arrangement of the device is obtained which can also be used with high exhaust gas temperatures, when temperature resistant light conductive bodies of glass are employed.

DRAWING

An embodiment example of the invention is shown in the drawing and is described below in more detail. FIG. 1 shows a simplified representation of the device in longitudinal section, and FIG. 2 shows a section of the device in accordance with FIG. 1 through II—II.

DESCRIPTION OF THE EMBODIMENT EXAMPLES

Figure 1:
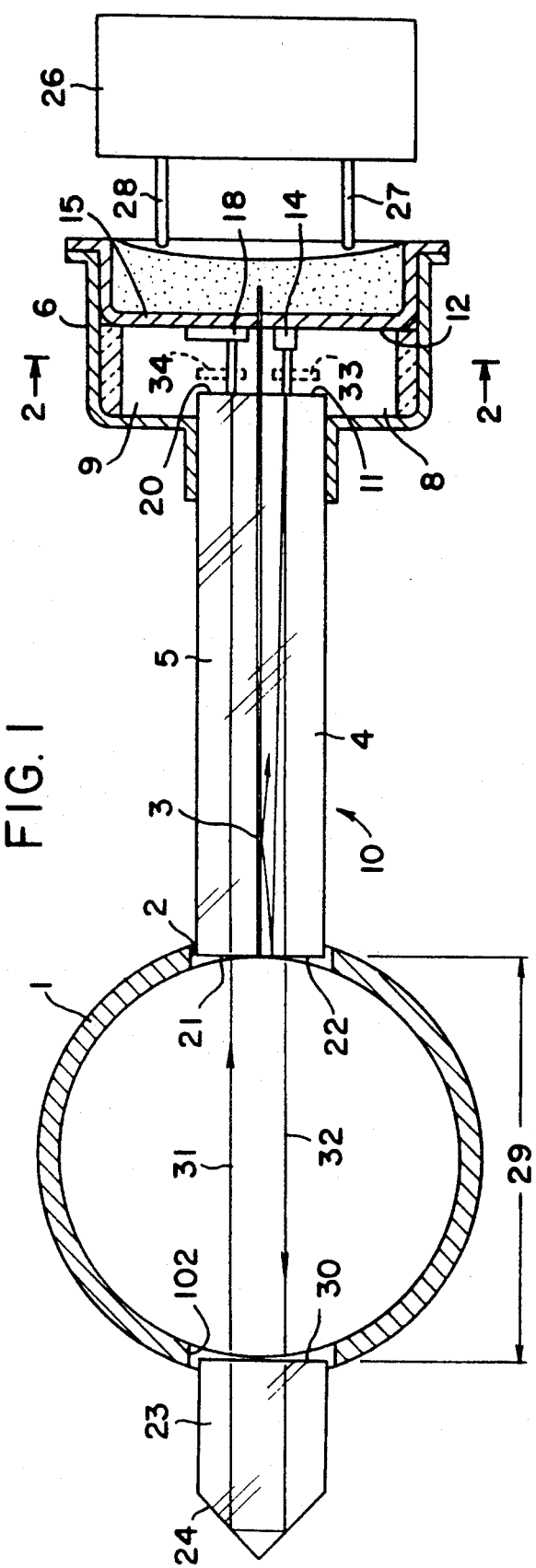
Figure 2:
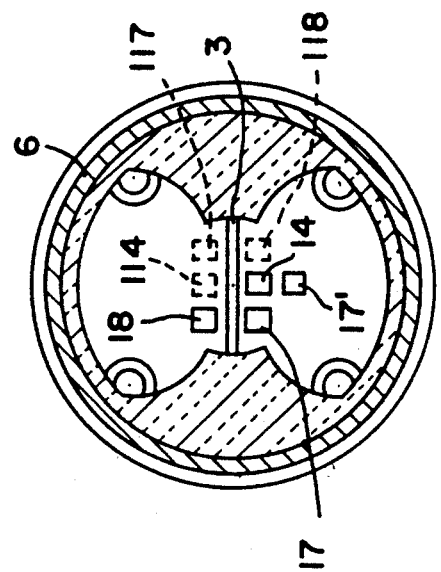

In FIG. 1, a section through an exhaust pipe 1 is shown, which is connected to the exhaust system of an internal combustion engine. Two diametrically opposed apertures 2 and 102 are provided in the exhaust pipe, from each of which a light conductive, bar shaped body leads off. This may consist of glass, glass fibre, or some other light conductive material. One light conductive body 10 is divided in two by an opaque layer 3, which may be a metal foil, a piece of sheet metal, or, in the section remote from the exhaust, an opaque layer or film of plastic, such that a bar shaped first light conductive body 4 and a second light conductive body 5 will be formed which extend in longitudinal direction, parallel to each other, and optically separated. At the end of the light conductive bodies 4, 5 which is remote from the exhaust pipe, these light conductive bodies terminate in a housing 6 which encloses in its light-tight interior a first chamber 8 and a second chamber 9. The housing, for example, may be of metal. The two chambers are partially separated, light-tight, by the end of the metal sheet 3 which is routed out of the end of the light conductive body, with the first light conductive body 4 terminating in the first chamber 8 and the second light conductive body 5 terminating in the second chamber 9. On the front wall 12 of the housing opposite face 11 of the first light conductive body 4 in the first chamber 8, a controllable light source 14 is arranged which serves as a light transmitter. This light source may be a light emitting diode which is arranged on a metal base 15, preferably aluminium or copper, which forms the front face 12. The section through the housing 6 in FIG. 2 shows that a reference light receiver 17, which may also be a light sensitive semiconductor, is provided in addition to the light source and arranged adjacent to the same. In addition to the one reference light receiver, at least one further reference light receiver 17' will preferably be provided. Light source 14 and reference light receivers 17, 17' are arranged close to and opposite the metal sheet 3. On the other side of the metal sheet in the second chamber 9, a light receiver 18 for the measured length is located, which is also arranged on the continuous metal base 15 and which is opposite the front face 20 of the second light conductive body 5, this front face pointing into the second chamber 9. On the side of the exhaust gas pipe 1, the first light conductive body 4 and the second light conductive body 5 point at right angles into the gas pipe interior in such a way that the front faces 21 and 22 terminate approximately at the inner diameter of the exhaust gas pipe. On the opposite side, the other light conductive body 23 leads off in the same way, it is designed as a reflecting arrangement with a retro-reflection face 24 in the form of a 90° cone.

In addition, the device is provided with an evaluation circuit 26 which is connected to the light source 14, the reference light receivers 17, 17', and the light receiver 18 for the measured length, via the line connections 27, 28.

During operation of the device, exhaust gas from an internal combustion engine flows through the exhaust gas pipe 1. This gas contains a concentration of components to be measured which may be harmful substances such as NOX, CH, CO, or other chemical compounds originating from the combustion, in particular particles of soot. Such constituents of gases will influence light which is sent through the exhaust gas, in such a way that certain proportions of the light absorb more or less intensely, depending on the characteristics of the impurities or the constituents of the exhaust gas. This change of the light sent through the exhaust gas which is caused by the cloudiness of the gas, makes it possible to draw conclusions from the resulting light, as to the constituents of the exhaust gas. It is possible not only to reduce the output intensity of the light, but also to change the spectral composition of the light due to certain absorption capabilities of the constituents in the exhaust gas. The evaluation circuit and the change of light in relation to the original condition allow, in a simple and contactless manner, the constituents in the exhaust gas to be determined, without any other analytical processes. In operation, the above described equipment is used to send a light ray 32 from the light source 14 vertically through the front face 11 into the first light conductive body 4, this ray re-emerging on the opposite front face 22 at right angles and progressing mainly diametrically through the exhaust pipe which forms a measured length 29 with its largest diameter at this point. Opposite, the light enters at right angles on the front face 30 of the other light conductive body 23 and is turned by 90° on the retro-reflection faces 24 of that body and is then again reflected back, offset by 180° in relation to its original direction, into the exhaust gas pipe 1. From there, the reflected light ray 31 enters at right angles into the front face 21 of the second light conductive body 5, passing through this, and entering on its front face 20 into the second chamber 9, where it falls onto the light receiver 18. The outgoing light ray 32 passes through the measured length 29 through which the reflected light ray 31 also passes. The change which the light ray undergoes in this path can now be ascertained in the receiver, as a light intensity which has changed in relation to the initial light intensity of the light source 14.

There are three options for achieving an accurate measured result. One consists of the starting light intensity of the light source being controlled to a constant value. For this purpose, the reference light receiver 17 is provided in the first chamber 8, which directly registers the radiated light intensity. In the evaluation circuit, the measured result of the reference light receiver is compared with a set-point value and, depending on the deviation from this set-point, the light emission of the light source is adjusted, for example, by increasing the current flow through the light emitting diode. In a light source thus controlled to a constant light emission, this light emission can be equated to a constituent-free gas in the exhaust pipe. The measured value which is then ascertained by the measured length light receiver 18 can be used directly as the measurement result for the degree of clouding or for the degree of loading of the exhaust gas with certain constituents.

Another method of achieving an accurate measurement result is that of controlling the adjustable light source by means of the result from the comparison between a set-point value and the output signal of the measured length light receiver. In this way, the output signal is held at a constant value, and the light emission of the light source ascertainable through the reference light receiver then corresponds to the degree of exhaust gas clouding and the degree of exhaust gas loading with certain constituents, respectively.

Finally, the measurement can also be carried out in such a way that the light source is not controlled, but that the initial light emission of the light source is ascertained by the reference light receiver, and the value given by that is compared with that of the measured length light receiver. The result of the comparison will then also provide an output value which corresponds to the exhaust gas clouding or the loading of the exhaust gas with constituents.

If the light ray is also used to check the exhaust gas for constituents which have a particular capacity for absorption of light within the range of certain light wavelengths, then the light source can produce its light emission predominantly within the range of these light waves in order to register just these constituents. This is done either by suitable selection of the light source which will then have a definite light spectrum, or, a filter 33 is arranged downstream from the light source, such as that shown by a dashed line in FIG. 1. In this case, the measured length light receiver 18 can have a definite sensitivity within the spectral range of the light, or it can be made especially sensitive towards it by a superposed filter 34. In certain cases, it will suffice that such a filter is provided on only one of the components, the light source, or the measured length light receiver. The reference light receiver allocated to the light source is then also equipped with such a filter.

Instead of arranging only one light source with a general light spectrum, it is possible, alternatively, to arrange several light sources, each with a specific light spectrum in their light emission. This also applies to the receiver side. One or several of these light sources and receivers can be operated simultaneously, depending on requirements. Via an appropriately designed evaluation circuit, the individual output values from the measured length light receivers and from the reference light receivers, respectively, can then be selectively evaluated.

FIG. 2 shows a refinement of the invention in which several reference light receivers 17 are allocated to the light source 14. With this allocation, the light emissions of the light source can be registered more accurately in an advantageous way inasmuch that their spacial radiation is taken into consideration. A second light source 114 and a second reference light receiver 117 are arranged in another chamber and the device includes a second measuring length light receiver 118.

In order to avoid the occurrence of drift during measuring, it is important that the temperatures of the reference light receiver and of the measured length light receiver are approximately equal. In order to achieve this in a simple manner, the light source and receiver are placed on the common metal base 15 which has good heat conducting properties and via which a temperature equalization takes place. It is further possible to arrange a light source, a reference light receiver, and a measured length light receiver in each of the chambers 8 and 9. The equipment is alternately operated in such a way that a light source and a reference light receiver is operated in one of the chambers while the measured length light receiver is in operation in the other one of the chambers. It is further possible, as an alternative, to provide only one light receiver in each of the chambers, and this receiver would serve as a reference light receiver on one occasion and as a measured length light receiver on another occasion, depending on the direction of measurement. In this way, temperature differences are equalized by the different operation of optoelectrical elements of different numbers in one chamber or another.

The above described designs with alternating operating modes can be equally well operated as described above, with upstream and downstream light filters, respectively, thereby making it possible to operate the previously described equipment not only alternately, but also simultaneously. The light source of the first chamber with its associated reference light receiver and measured length light receiver is then always equipped with the same filter, which will however have a different spectral translucence from those filters with which the light source of the second chamber with the associated reference and measuring light receivers are equipped.

The described equipment enables the constituents of exhaust gas to be very accurately maintained within wide limits. Drift occurrences, in particular, will be kept very low. This is due to the fact that a temperature equalization takes place, via the metal base with good thermal conductivity, between the optoelectrical construction elements, and also due to the fact that two of the optoelectrical construction elements are operated at any one time, once on the one side and once on the other side, or even simultaneously. The structural size of the device is small and compact, and its application is universal.

We claim:

1. Device for measuring the composition of fluids, in particular the constituents of exhaust gases of internal combustion engines, comprising: a light source, a first light conductive body for passing light supplied by said source, a measuring length for receiving the supplied light and exposed to a fluid, a reflective arrangement provided at the end of the measuring length through which supplied light is reflected through the fluid, a second light conductive body which is optically separated from the first light conductive body and for passing the reflected light, a measuring length light receiver downstream from said second light conductive body, a chamber which is shielded light-tight but is connected with the first light conductive body, a reference light receiver, both said light source and said reference light receiver being arranged together within said chamber, said reference light receiver being directly exposed to the light emitted by said light source, a metallic separating level, the first light conductive body and the second light conductive body comprising a light conductor divided into two optical longitudinal columns by the metallic separating level, a light-tight shielded housing which is divided into two chambers which are separated from each other in a light-tight manner by a part of the separating level protruding from the light conductor, one of these chambers being said chamber having said light source and said reference light receiver arranged therein and the other of these chambers having disposed therein at least one light receiver, said light source and the light receivers being connected with each other in a thermally conductive way.

2. Device in accordance with claim 1, in which the said light receivers are connected with an evaluation circuit, through which circuit a signal corresponding to the composition of the fluid can be produced, in which device the output signals of the light receivers are connected to the input of a comparator device which is further connected to a set-point generator and on the output side to a control device for the control of the light emission from the light source.

3. Device in accordance with claim 1, in which output signals of the reference and measuring length light receivers are connected to an evaluation circuit means for comparing with each other the output signals of the reference and measuring length light receivers and for correcting the value of the output signal of the measuring length light receiver in accordance with the value of the output signal of the reference length light receiver in order to produce an output signal which corresponds to the composition of the fluid.

4. Device in accordance with claim 1, in which reference light receiver (17) consists of several individual reference light receivers (17, 17') which are arranged around the light source (14).

5. Device in accordance with claim 1, which includes in addition to the light source and the reference light receiver arranged in said one of said chambers which is exposed to an input side of the first light conductive body and which device includes in addition to said measuring length light receiver a second light source and a second reference light receiver arranged in said other chamber, a second measuring length light receiver which is exposed to an output side of the second light conductive body, said second measuring length light receiver, said second light source, and said second reference light receiver being operated alternately to said light source, said measuring length light receiver and said reference light receiver.

6. Device in accordance with claim 1, in which the second light conductive body terminates on an output side also in said light-tight shielded other chamber, and which device includes additionally to the measuring length light receiver a second light source, in which the light sources are operated alternately and the light receivers are operated alternately as reference light receivers or as measuring length light receivers, so that one reference light receiver is always assigned to the light source being operated.

7. Device in accordance with claim 1, in which the light source comprises several individual light sources of different light wavelength emission and the light receivers comprise several individual light receivers with different light wavelength sensitivity.

8. Device in accordance with claim 7, which includes optical filters arranged downstream from the light source and upstream from the light receivers for the generation of the different light wavelength emission or sensitivity.

* * * * *